(12) United States Patent
Reo et al.

(10) Patent No.: US 7,101,888 B2
(45) Date of Patent: Sep. 5, 2006

(54) ORAL LIQUID TOLTERODINE COMPOSITION

(75) Inventors: Joseph P. Reo, Kalamazoo, MI (US); Kathryn M. Kienle, Kalamazoo, MI (US); Jennifer K. Fredrickson, Kalamazoo, MI (US)

(73) Assignee: Pharmacia & UpJohn Company, Kalamazoo, MI (US)

( * ) Notice: Subject to any disclaimer, the term of this patent is extended or adjusted under 35 U.S.C. 154(b) by 230 days.

(21) Appl. No.: 10/647,816

(22) Filed: Aug. 25, 2003

(65) Prior Publication Data

US 2005/0032905 A1 Feb. 10, 2005

Related U.S. Application Data

(60) Provisional application No. 60/406,429, filed on Aug. 28, 2002.

(51) Int. Cl.
*A01N 43/90* (2006.01)
*A61K 31/519* (2006.01)

(52) U.S. Cl. .............. 514/261.1; 514/261.1; 514/254

(58) Field of Classification Search .......... 514/648, 514/649, 555
See application file for complete search history.

(56) References Cited

U.S. PATENT DOCUMENTS

| 5,922,914 A | * | 7/1999 | Gage et al. | 564/413 |
| 2003/0060513 A1 | * | 3/2003 | Americ et al. | 514/648 |
| 2003/0199582 A1 | * | 10/2003 | Hawley et al. | 514/555 |

OTHER PUBLICATIONS

Pediatric Pharmacotherapy A Monthy News letter for Health Care Professionals Children's Medical Center at the University of Virginia vol. 2 No. 9 Sep. 1996.*

* cited by examiner

*Primary Examiner*—Christopher S. F. Low
*Assistant Examiner*—Shirley V. Gembeh
(74) *Attorney, Agent, or Firm*—Gregg C. Benson; Carl J. Goddard (57) ABSTRACT

A pharmaceutical composition in a form of an orally deliverable liquid comprises water having in solution therein a pharmaceutically acceptable water-soluble salt of a tolterodine related compound at a therapeutically effective concentration in the composition. The composition has a pH of about 2 to about 6 and further comprises a sweetening agent and an antimicrobial agent at a concentration that is antimicrobially effective at the pH of the composition. The composition is useful for treating a muscarinic receptor mediated disorder, more particularly overactive bladder, in a subject by orally administering to the subject a therapeutically effective amount of the composition.

30 Claims, 1 Drawing Sheet

Fig. 1

ORAL LIQUID TOLTERODINE COMPOSITION

This application claims priority of U.S. provisional application Ser. No. 60/406,429 filed on Aug. 28, 2002.

FIELD OF THE INVENTION

The present invention relates to pharmaceutical formulations of an antimuscarinic drug, more specifically tolterodine, suitable for oral administration for treatment of muscarinic receptor mediated disorders. In particular, it relates to such formulations in liquid form.

BACKGROUND OF THE INVENTION

Overactive bladder, a disorder affecting millions of individuals, including children as well as adults, worldwide, is characterized by urge urinary incontinence, urinary urgency and frequency. This disorder is a significant cause of anxiety and distress to those affected. Overactive bladder arises from abnormal activity of the detrusor muscle and can be idiopathic or neurogenic in origin.

Idiopathic cases are characterized by detrusor instability, resulting in involuntary bladder contractions when sensory impulses to the bladder are increased. A variety of conditions, including lower urinary tract infections, atrophic vaginitis, fecal impact and prostatic hypertrophy, can increase such impulses to the bladder, leading to bladder contractions. Cases due to neurological dysfunction are characterized by detrusor hyperreflexia and can be associated for example with cerebrovascular accident, Alzheimer's disease, tumors of the central nervous system, multiple sclerosis, spina bifida, Parkinson's disease, spinal cord damage and spinal dysraphism.

Involuntary contractions of the detrusor muscle, like the physiological contractions associated with normal voiding processes, are mediated by acetylcholine-induced stimulation of muscarinic receptors. Muscarinic receptor antagonists (antimuscarinics), have accordingly become a mainstay of treatment for overactive bladder. A widely prescribed antimuscarinic in treatment of overactive bladder is oxybutynin, typically in the form of its hydrochloride salt ("oxybutynin chloride"). Unfortunately the adverse effects of oxybutynin, for example dry mouth, loss of visual accommodation, palpitations and constipation, can lead to poor patient compliance and discontinuation of treatment. It is noted that saliva flow, which when reduced causes dry mouth, is also muscarinic receptor mediated, and is thus a particularly common adverse effect of antimuscarinics.

The more recently introduced drug tolterodine (I), an antimuscarinic developed specifically for treatment of overactive bladder, has affinity for the muscarinic receptors of the salivary gland that is about eight times lower than that of oxybutynin. Tolterodine is commercially available as the tartrate salt under the trade name Detrol® and other trademarks of Pharmacia & Upjohn.

(I)

Synthesis of tolterodine is disclosed in the patents individually cited below and incorporated herein by reference.

U.S. Pat. No. 5,382,600.
U.S. Pat. No. 5,559,269.
U.S. Pat. No. 5,686,464.
U.S. Pat. No. 5,922,914.

Tolterodine is commercially available as an immediate-release formulation (Detrol® tablets) suitable for twice daily administration, and an extended-release formulation (Detrol® LA capsules) suitable for once daily administration. See for example *Physicians' Desk Reference*, 57th ed. (2003), pp. 2735–2740. Certain subjects, in particular children but also many adults, often have difficulty in swallowing tablets or capsules. It is therefore desirable to have a liquid tolterodine composition that can be orally administered to such subjects.

Tablets and capsules are typically swallowed without significant interaction with taste and other sensors in the mouth. By contrast, liquid formulations do not escape such sensors, and in developing an oral liquid formulation such factors as taste and astringency must be taken into account. Unpleasant tasting and/or astringent compositions can lead to patient noncompliance and discontinuation, especially amongst pediatric populations.

Another attendant difficulty with liquid formulations is their potential instability, both physical and chemical. Tolterodine exhibits chemical instability in aqueous media at neutral to alkaline pH levels. Instability can also result from microbial activity, thus it is usually necessary to include an antimicrobial agent in such formulations. Many antimicrobial agents do not function well at the low pH levels where chemical stability of tolterodine is maximized.

Oxybutynin hydrochloride is commercially available as an oral liquid formulation, for example as Ditropan® syrup of Alza Corp. This formulation is an aqueous solution of oxybutynin hydrochloride, sucrose, sorbitol, glycerin, citric acid, sodium citrate, methylparaben, coloring and flavoring.

Ditropan® syrup and generic oxybutynin chloride oral liquid formulations do not overcome the adverse effects of oxybutynin noted above and, furthermore, do not exhibit good palatability in taste testing.

Therefore, it is an object of the present invention to provide an orally deliverable liquid composition for treatment of a muscarinic receptor mediated disorder, in particular overactive bladder, having a superior side-effect profile to liquid oxybutynin chloride formulations.

It is a further object to provide an orally deliverable liquid formulation of tolterodine having improved palatability over commercially available liquid formulations of oxybutynin chloride, for example in respect of taste and/or astringency.

It is a still further object to provide an orally deliverable liquid formulation of tolterodine that exhibits good stability and good resistance to microbial activity.

SUMMARY OF THE INVENTION

There is now provided a pharmaceutical composition in a form of an orally deliverable liquid, the composition comprising water having in solution therein a pharmaceutically acceptable water-soluble salt of a tolterodine related compound at a therapeutically effective concentration in the composition. The composition has a pH of about 2 to about 6 and further comprises a sweetening agent and an antimicrobial agent at a concentration that is antimicrobially effective at the pH of the composition.

Such a composition has been found to satisfy one or more of the objects set forth above and to present other benefits and advantages disclosed hereinbelow.

A "tolterodine related compound" herein is tolterodine, (R)-N,N-diisopropyl-3-(2-hydroxy-5-methylphenyl)-3-phenylpropanamine, its (S)-enantiomer or a racemic mixture thereof; a metabolite thereof that exhibits antimuscarinic activity, including (R)-N,N-diisopropyl-3-(2-hydroxy-5-hydroxymethylphenyl)-3-phenylpropanamine (herein "hydroxytolterodine"), its (S)-enantiomer or a racemic mixture thereof; or a prodrug of tolterodine, hydroxytolterodine, their (S) enantiomers or racemic mixtures. A preferred such compound is tolterodine.

A "water-soluble salt" herein is one having sufficient solubility in water to exist in solution at a therapeutically effective concentration in the composition. Typically, the salt has a solubility in water of at least about 1 mg/ml, preferably at least about 10 mg/ml.

A "therapeutically effective concentration" of a tolterodine related compound in the composition is a concentration such that a therapeutically effective amount of the compound is present in a suitable dosage volume of the composition, preferably a volume not greater than about 20 ml. Typically the compound is present at a concentration of about 0.01 to about 1 mg/ml.

A "therapeutically effective amount" of a tolterodine related compound is an amount sufficient to elicit a therapeutic response in a subject when administered orally as part of an established dosage regimen. Typically a therapeutically effective amount of the compound is about 0.2 to about 5 mg, preferably about 1 to about 2 mg, administered 1–2 times daily.

There is further provided a method for treating a muscarinic receptor mediated disorder, more particularly overactive bladder, in a subject by orally administering to the subject a therapeutically effective amount of a composition as herein described.

There is still further provided a method of use of a composition as herein described in manufacture of a medicament for treatment of a muscarinic receptor mediated disorder, more particularly overactive bladder.

DETAILED DESCRIPTION OF THE INVENTION

A composition of the invention is an orally deliverable aqueous liquid having a water-soluble salt of a tolterodine related compound as active agent in solution therein. The compound is typically present at a concentration of about 0.01 to about 1 mg/ml in the composition as a whole, preferably about 0.05 to about 0.8 mg/ml, and most preferably about 0.1 to about 0.4 mg/ml. A particularly useful illustrative concentration is about 0.2 mg/ml, providing a unit dose of about 1 mg of the compound in a 5 ml dosage volume, or about 2 mg of the compound in a 10 ml dosage volume. Concentrations and dosage amounts herein are expressed as salt, for example tolterodine tartrate, not as free base equivalent, unless otherwise specified.

In one embodiment the compound is hydroxytolterodine.

In a presently preferred embodiment the compound is tolterodine.

Suitable salts of the tolterodine related compound, in particular of tolterodine, include those prepared from acids selected from aliphatic $C_{7-24}$ mono- and dicarboxylic acids, e.g., heptanoate, caprate and laurate; $C_{2-4}$ alkanedisulfonic acids, e.g., 1,2-ethanedisulfonate (edisylate), $C_{11-27}$ naphthoic acid derivatives, e.g., 4,4'-methylenebis(3-hydroxy-2-naphthoate) (pamoate), 1-hydroxy-2-naphthoate (xinafoate) and 2-hydroxy-1-naphthoate; maleate, fumarate, benzoate, tartrate, hydrochloride, hydrobromide, hydroiodide, sulfate, phosphate, nitrate, citrate, methanesulfonate (mesylate), and the like, so long as they meet the solubility criteria provided herein.

Particularly preferred is the tartrate salt of tolterodine. Normally the L-tartrate is used.

The composition has a pH of about 2 to about 6, preferably about 3 to about 5, more preferably about 3.5 to about 4.5, for example about 4. Any pharmaceutically acceptable means of adjusting pH to such a level can be used, for example inclusion in the composition of a pharmaceutically acceptable acid such as acetic, citric, fumaric, hydrochloric, lactic or nitric acids or the like, or a mixture thereof. It will also be understood that certain compositions of the invention can have a pH in the desired range without inclusion of a pH adjusting agent specifically for that purpose. Typically, however, an acidic buffer system is present in the composition to achieve the desired pH.

An acidic buffer system comprises an acidulant and a buffering agent. Suitable acidulants will be known to those of skill in the art and illustratively include acetic, citric, fumaric, hydrochloric, lactic and nitric acids and the like, and mixtures thereof. Suitable buffering agents will likewise be known to those of skill in the art and illustratively include potassium metaphosphate, potassium phosphate, sodium acetate, sodium citrate and the like, and mixtures thereof.

In a preferred embodiment, the acidic buffer system comprises an acidulant acid and an alkali metal salt of the same acid. Particularly preferred is an acidic buffer system comprising citric acid and sodium citrate. Illustratively, citric acid can be present at a concentration of about 3 to about 10 mg/ml, preferably about 4 to about 7 mg/ml, for example about 5 mg/ml; and sodium citrate can be present at a concentration of about 3 to about 8 mg/ml, preferably about 4 to about 7 mg/ml, for example about 6 mg/ml.

The antimicrobial agent is selected to be antimicrobially effective at the pH of the composition, and an antimicrobially effective amount of the agent is present. Suitable agents can illustratively be selected from sorbic and benzoic acids and salts thereof, particularly the sodium and potassium salts, p-hydroxybenzoic acid esters such as methylparaben, and mixtures thereof. Suitable concentrations can be established by one of skill in the art by testing, as illustrated in Example 16 for sodium benzoate, and will generally be found in a range of about 0.1 to about 5 mg/ml, depending on the agent selected.

An illustrative preferred antimicrobial agent is sodium benzoate, at a concentration in the composition of at least about 0.6 mg/ml, preferably at least about 1 mg/ml. Illustratively, the concentration of sodium benzoate is about 0.6 to about 2 mg/ml, for example about 0.7 to about 1.5 mg/ml.

The composition also comprises a sweetening agent (sweetener). Any pharmaceutically acceptable sweetening agent can be used, including natural and synthetic sugars and other synthetic sweeteners.

Suitable sugars illustratively include glucose, fructose, sucrose, xylitol, tagatose, sucralose, maltitol, isomaltulose, Isomalt™ (hydrogenated isomaltulose), lactitol, sorbitol, mannitol, trehalose, maltodextrin, polydextrose, etc. Other sweeteners illustratively include glycerin, erythritol, maltol, acesulfame and salts thereof, e.g., acesulfame potassium, alitame, aspartame, neotame, cyclamate, saccharin and salts thereof, e.g., saccharin sodium, neohesperidin dihydrochalcone, stevioside, thaumatin, etc. Sweeteners can be used in the form of crude or refined products such as hydrogenated starch hydrolysates, maltitol syrup, high fructose corn syrup, etc., and as branded products, e.g., Sweet Am™ liquid (Product Code 918.003—propylene glycol, ethyl alcohol, and proprietary artificial flavor combination) and Sweet Am™ powder (Product Code 918.005—maltodextrin, sorbitol, and fructose combination and Product Code 918.010—water, propylene glycol, sorbitol, fructose, and proprietary natural and artificial flavor combination) of Flavors of North America, ProSweet™ (1–10% proprietary plant/vegetable extract and 90–99% dextrose combination) of Virginia Dare, Maltisweet™ (maltitol solution) and Sorbo™ (sorbitol and sorbitol/xylitol solution) of SPI Polyols and Invertose™ (high fructose corn syrup) of Corn Products International. Sweeteners can be used singly or in combinations of two or more.

Suitable concentrations of different sweeteners can be selected by those of skill in the art based on published information, manufacturers' data sheets, etc., and by routine testing. Illustratively, Sweet Am™ liquid or powder or a product substantially equivalent thereto can be present at about 0.1 to about 50 mg/ml, preferably about 0.1 to about 5 mg/ml, more preferably about 0.1 to 1 mg/ml, still more preferably about 0.2 to about 0.8 mg/ml, and most preferably about 0.3 to about 0.6 mg/ml. Illustratively, fructose can be present at about 200 to about 300 mg/ml, preferably about 240 to about 290 mg/ml, and most preferably about 250 to about 280 mg/ml. Illustratively glucose (dextrose) can be present at about 5 to about 300 mg/ml, preferably about 5 to about 50 mg/ml, more preferably about 10 to about 30 mg/ml, and most preferably about 15 to about 25 mg/ml. Illustratively, sorbitol can be present at about 20 to about 300 mg/ml, preferably about 20 to about 80 mg/ml, more preferably about 30 to about 70 mg/ml, and most preferably about 40 to about 60 mg/ml. Concentrations outside the ranges presented herein can also be useful.

In a preferred embodiment, the composition also comprises a flavoring agent (flavorant). A "flavoring agent" herein is a substance capable of enhancing taste or aroma of a composition. Suitable natural or synthetic flavoring agents can be selected from standard reference books, for example *Fenaroli's Handbook of Flavor Ingredients*, 3rd edition (1995). Non-limiting examples of suitable natural flavors, some of which can readily be simulated with synthetic agents or combinations thereof, include almond, anise, apple, apricot, bergamot, blackberry, blackcurrant, blueberry, cacao, caramel, cherry, cinnamon, clove, coffee, coriander, cranberry, cumin, dill, *eucalyptus*, fennel, fig, ginger, grape, grapefruit, guava, hop, lemon, licorice, lime, malt, mandarin, molasses, nutmeg, orange, peach, pear, peppermint, pineapple, raspberry, rose, spearmint, strawberry, tangerine, tea, vanilla, wintergreen, etc. Also useful, particularly where the composition is intended primarily for pediatric use, is tutti-frutti or bubblegum flavor, a compounded flavoring agent based on fruit flavors. Presently preferred flavoring agents include anise, cinnamon, cacao, orange, peppermint, cherry (in particular wild cherry), grape, bubblegum and vanilla. Wild cherry is particularly preferred. Flavoring agents can be used singly or in combinations of two or more.

Typically the flavoring agent, or an oil or essence comprising the flavoring agent, if present is at a concentration in the composition of about 0.1 to about 5 mg/ml, preferably about 0.2 to about 3 mg/ml, and most preferably about 0.5 to about 2 mg/ml.

Optionally, the composition further comprises a coloring agent. Suitable coloring agents illustratively include FD&C Red No. 3, FD&C Red No. 20, FD&C Red No. 40, FD&C Yellow No. 6, FD&C Blue No. 2, D&C Green No. 5, D&C Orange No. 5, caramel, ferric oxide and mixtures thereof. Illustratively, FD&C Red # 40 is present at a concentration in the composition of 0 to about 3 mg/ml, preferably 0 to about 2 mg/ml, and most preferably 0 to about 1 mg/ml.

A composition of the invention can be used in treatment of muscarinic receptor mediated disorders such as urinary disorders including overactive bladder, by orally administering to a subject in need thereof a therapeutically effective amount of the composition. It is contemplated that the composition can also be used to treat other disorders including asthma, chronic obstructive pulmonary disease (COPD), allergic rhinitis, and rhinorrhea due to the common cold.

EXAMPLES

Example 1

A composition as set forth in Table 1 was prepared as described below. In this and following Examples, it will be understood that, for clarity and comparative purposes, compositions are described as having a total volume of 1 ml, even where larger volumes were actually made, and that other volumes can be made by varying the amounts of the ingredients pro rata. Amounts of ingredients comprising water are expressed as gross weight, including water, not on a solids-only basis.

TABLE 1

Composition of Example 1 of the invention

| Ingredient | Amount (mg) |
|---|---|
| tolterodine L-tartrate | 0.2 |
| sucrose solution (85% solids) | 382.42 |
| sorbitol solution[1] (70% solids) | 54 |
| citric acid | 5.88 |
| sodium citrate | 5 |
| sodium benzoate | 1 |
| artificial wild cherry flavor | 1 |
| Sweet Am ™ powder | 0.5 |
| purified water | q.s. to 1 ml |

[1]Sorbo ™ of SPI Polyols

The composition was prepared by adding the tolterodine salt and a portion of the water to a volumetric flask, followed by agitation until the tolterodine salt was fully dissolved. Next, the citric acid, sodium citrate and sodium benzoate were added to the flask and dissolved. The wild cherry flavoring and Sweet A™ were subsequently added to the flask and mixed as well. The sucrose and sorbitol solutions were then added to the flask and mixed thoroughly. Finally, water was added to the flask with mixing to provide the finished composition, which had a pH of 4.0.

Example 2

A composition as set forth in Table 2 was prepared as in Example 1. The composition had a pH of 4.0.

TABLE 2

Composition of Example 2 of the invention

| Ingredient | Amount (mg) |
|---|---|
| tolterodine L-tartrate | 0.2 |
| sorbitol solution[1] (70% solids) | 314.42 |
| maltitol solution[2] (70% solids) | 122 |
| citric acid | 5.88 |
| sodium citrate | 5 |
| sodium benzoate | 1 |
| artificial wild cherry flavor | 1 |
| Sweet Am ™ powder | 0.5 |
| purified water | q.s. to 1 ml |

[1] Sorbo ™ of SPI Polyols
[2] Maltisweet ™ of SPI Polyols

Example 3

A composition as set forth in Table 3 was prepared as in Example 1. The composition had a pH of 4.0.

TABLE 3

Composition of Example 3 of the invention

| Ingredient | Amount (mg) |
|---|---|
| tolterodine L-tartrate | 0.2 |
| high fructose corn syrup[1] (77% solids) | 382.42 |
| sorbitol solution[2] (70% solids) | 54 |
| citric acid | 5.88 |
| sodium citrate | 5 |
| sodium benzoate | 1 |
| artificial wild cherry flavor | 1 |
| Sweet Am ™ powder | 0.5 |
| purified water | q.s. to 1 ml |

[1] Invertose ™ of Corn Products International
[2] Sorbo ™ of SPI Polyols

Example 4

A composition as set forth in Table 4 was prepared as in Example 1. The composition had a pH of 4.0.

TABLE 4

Composition of Example 4 of the invention

| Ingredient | Amount (mg) |
|---|---|
| tolterodine L-tartrate | 0.2 |
| high fructose corn syrup[1] (77% solids) | 382.4 |
| sorbitol | 54 |
| citric acid | 5.88 |
| sodium citrate | 5 |
| sodium benzoate | 1 |
| artificial wild cherry flavor | 1 |
| Sweet Am ™ powder | 0.5 |
| purified water | q.s. to 1 ml |

[1] Invertose ™ of Corn Products International

Example 5

A composition as set forth in Table 5 was prepared as in Example 1. The composition had a pH of 4.0.

TABLE 5

Composition of Example 5 of the invention

| Ingredient | Amount (mg) |
|---|---|
| tolterodine L-tartrate | 0.2 |
| fructose | 265 |
| dextrose | 20.61 |
| sorbitol | 54 |
| citric acid | 5.88 |
| sodium citrate | 5 |
| sodium benzoate | 1 |
| artificial wild cherry flavor | 1 |
| Sweet Am ™ powder | 0.475 |
| purified water | q.s. to 1 ml |

Example 6

A composition as set forth in Table 6 was prepared as in Example 1. The composition had a pH of 4.0.

TABLE 6

Composition of Example 6 of the invention

| Ingredient | Amount (mg) |
|---|---|
| tolterodine L-tartrate | 0.2 |
| fructose | 265 |
| dextrose | 20.61 |
| sorbitol | 54 |
| citric acid | 5.88 |
| sodium citrate | 5 |
| sodium benzoate | 1 |
| FD&C Red No. 40 | 0.1 |
| artificial wild cherry flavor | 1 |
| Sweet Am ™ powder | 0.475 |
| purified water | q.s. to 1 ml |

Example 7

A composition as set forth in Table 7 was prepared as in Example 1. The composition had a pH of 4.0.

TABLE 7

Composition of Example 7 of the invention

| Ingredient | Amount (mg) |
|---|---|
| tolterodine L-tartrate | 0.2 |
| high fructose corn syrup[1] (77% solids) | 382.4 |
| sorbitol | 54 |
| citric acid | 5.88 |
| sodium citrate | 5 |
| sodium benzoate | 1 |
| purified water | q.s. to 1 ml |

[1] Invertose ™ of Corn Products International

Example 8

A composition as set forth in Table 8 was prepared as in Example 1. The composition had a pH of 4.0.

TABLE 8

Composition of Example 8 of the invention

| Ingredient | Amount (mg) |
| --- | --- |
| tolterodine L-tartrate | 0.2 |
| high fructose corn syrup[1] (77% solids) | 382.4 |
| sorbitol | 54 |
| citric acid | 5.88 |
| sodium citrate | 5 |
| sodium benzoate | 1 |
| artificial wild cherry flavor | 1 |
| purified water | q.s. to 1 ml |

[1]Invertose ™ of Corn Products International

Example 9

A composition as set forth in Table 9 was prepared as in Example 1. The composition had a pH of 4.0.

TABLE 9

Composition of Example 9 of the invention

| Ingredient | Amount (mg) |
| --- | --- |
| tolterodine L-tartrate | 0.2 |
| high fructose corn syrup[1] (77% solids) | 382.4 |
| sorbitol | 54 |
| citric acid | 5.88 |
| sodium citrate | 5 |
| sodium benzoate | 1 |
| artificial wild cherry flavor | 1 |
| Sweet Am ™ powder | 15 |
| purified water | q.s. to 1 ml |

[1]Invertose ™ of Corn Products International

Example 10

A composition as set forth in Table 10 was prepared as in Example 1. The composition had a pH of 4.0.

TABLE 10

Composition of Example 10 of the invention

| Ingredient | Amount (mg) |
| --- | --- |
| tolterodine L-tartrate | 0.2 |
| high fructose corn syrup[1] (77% solids) | 382.4 |
| sorbitol | 54 |
| citric acid | 5.88 |
| sodium citrate | 5 |
| sodium benzoate | 1 |
| artificial wild cherry flavor | 1 |
| ProSweet ™ liquid | 15 |
| purified water | q.s. to 1 ml |

[1]Invertose ™ of Corn Products International

Example 11

A composition as set forth in Table 11 was prepared as in Example 1. The composition had a pH of 4.0.

TABLE 11

Composition of Example 11 of the invention

| Ingredient | Amount (mg) |
| --- | --- |
| tolterodine L-tartrate | 0.2 |
| sorbitol | 54 |
| citric acid | 5.88 |
| sodium citrate | 5 |
| sodium benzoate | 1 |
| artificial wild cherry flavor | 1 |
| Sweet Am ™ powder | 0.5 |
| acesulfame K | 2.5 |
| aspartame | 2.5 |
| purified water | q.s. to 1 ml |

Example 12

A composition as set forth in Table 12 was prepared as in Example 1. The composition had a pH of 4.0.

TABLE 12

Composition of Example 12 of the invention

| Ingredient | Amount (mg) |
| --- | --- |
| tolterodine L-tartrate | 0.2 |
| sorbitol | 54 |
| citric acid | 5.88 |
| sodium citrate | 5 |
| sodium benzoate | 1 |
| artificial wild cherry flavor | 1 |
| Sweet Am ™ powder | 0.5 |
| acesulfame K | 7.5 |
| aspartame | 7.5 |
| purified water | q.s. to 1 ml |

Example 13

A composition as set forth in Table 13 was prepared as in Example 1. The composition had a pH of 4.0.

TABLE 13

Composition of Example 13 of the invention

| Ingredient | Amount (mg) |
| --- | --- |
| tolterodine L-tartrate | 0.2 |
| sorbitol | 54 |
| citric acid | 5.88 |
| sodium citrate | 5 |
| sodium benzoate | 1 |
| artificial wild cherry flavor | 1 |
| Sweet Am ™ powder | 0.5 |
| saccharin Na | 0.5 |
| purified water | q.s. to 1 ml |

Example 14

A composition as set forth in Table 14 was prepared as in Example 1. The composition had a pH of 4.0.

TABLE 14

Composition of Example 14 of the invention

| Ingredient | Amount (mg) |
| --- | --- |
| tolterodine L-tartrate | 0.2 |
| sorbitol | 54 |
| citric acid | 5.88 |
| sodium citrate | 5 |
| sodium benzoate | 1 |
| artificial wild cherry flavor | 1 |
| Sweet Am ™ powder | 0.5 |
| saccharin Na | 2.5 |
| purified water | q.s. to 1 ml |

Example 15

Palatability of the composition of Example 5 of the invention was evaluated along with the following comparators: Ditropan® syrup (Alza Corp.), generic oxybutynin chloride syrup (Morton Grove Pharmaceuticals, Inc.), Children's Tylenol® Cold plus Cough syrup (acetaminophen, dextromethorphan, hydrobromide, pseudoephedrine hydrochloride combination; McNeil), and Children's Benadryl® Allergy liquid (diphenhydramine hydrochloride; Warner-Lambert). The Ditropan® and generic oxybutynin chloride comparators were included as state of the art liquid medications for treatment of overactive bladder. The Tylenol® and Benadryl® comparators were included as examples of liquid medications used for other purposes but known to have highly acceptable palatability.

Samples of each composition were evaluated by a trained panel using the Profile Attribute Analysis (PAA) method. PAA generates highly reproducible data.

The trained panel numerically describes a complete sensory experience through profile attributes. These attributes are a limited set of characteristics which, when properly selected and defined, provide a complete objective description of the sensory characteristics of a sample with little descriptive information lost. Additional detail is provided by panel comments, which are stored in association with the attribute data. PAA data can be efficiently stored in automated data handling systems and is amenable to statistical analysis and data summarization.

The sensory or perceptual characteristics of a food or beverage are multi-variant. That means there are a variety of ways in which people distinguish among samples. These perceptions may be grouped into two sets—integrative and analytic.

Integrative perceptions can be measured as the overall aroma and flavor impression of a food or beverage. Integrative perceptual attributes such as "balance" and "fullness" are an essential part of the product description. Not only do these attributes distinguish among samples, they closely correlate with consumers' descriptions of products. Additional integrative measures such as total intensity of flavor, complexity, impact and aftertaste may be necessary to differentiate among samples.

Analytic perceptions include three chemical senses: smell, taste and mouthfeel. Each of these three chemical senses can be distinguished in terms of strength, quality and time. Visual and tactile perceptions also provide data that differentiate among samples and, like the chemical senses, can have more than one perceptual dimension.

PAA measures each sensory attribute on a seven-point scale (1–7). These measures express perceptual differences from a reference and are relative to a standard. Each point on the scale relative to an adjacent point represents a difference the panelists can detect with confidence on repeated analyses. On the scale a low rating represents zero or weak expression, and a high rating represents strong expression of the attribute.

To identify the specific attributes important to a particular range of products, the trained panel initially holds orientation sessions. The panel is presented with a wide variety of products that span the range of sensory differences to be included in the actual study. The panelists characterize the sensory properties of these products using descriptive analysis. From this characterization, the profile attributes necessary to completely describe the range of products are selected.

The following attributes can be included.

"Viscosity" refers to an attribute that measures the force required to draw a liquid from a spoon over the tongue. On the seven-point scale, 1 is referenced by water ("thin"), and 7 is referenced by sweetened condensed milk ("thick").

"Balance" refers to a measure of the degree of blend of character notes in the flavor complex.

"Fullness" refers to the body of flavor or degree of complexity.

"Aromatics" refers to an attribute that measures strength and type of flavors perceived in the olfactory area.

"Sweet" refers to an attribute that is a measure of intensity of sweet basic taste. The reference standards are sucrose solutions.

"Sour" refers to an attribute that is a measure of intensity of sour basic taste. The reference standards are citric acid solutions.

"Bitter" refers to an attribute that is a measure of intensity of bitter basic taste. The reference standards are caffeine solutions.

"Mouth irritation" refers to an attribute that measures trigeminal effects such as numbing, tongue sting and throat burn, i.e., irritation effects in the mouth or throat.

"Mouth feel" refers to an attribute that measures additional trigeminal effects such as synthetic sweetener sensation, chalky mouthfeel, astringent, or cooling.

"Others" refers to an attribute that includes basic tastes or aromatics (often off-flavors) that are not measured in any of the previous attributes. These can include sulfidy, waxy, green-stemmy, woody or paraben aromatics.

"Aftertaste" refers to measurement of selected attributes at specified intervals of time after swallowing. Aftertaste can include basic tastes such as sweet and bitter, off-flavors and aromatics.

Four or five panelists participated on each panel session and samples were evaluated according to the following protocol. Each panelist was given 2 ml of each test product. The 2 ml volume was swished in the mouth for about 10 seconds then expelled from the mouth. An initial flavor evaluation was made during swishing. An evaluation of aftertaste was then made at five time intervals: immediately, 1, 3, 5 and 10 minutes after expelling from the mouth. Panelists used spring water and unsalted crackers to rinse their mouths between samples. A 15 minutes washout period was provided between samples. Three samples were tasted at each session, with panelists participating in no more than two panel sessions per day.

Figure 1:
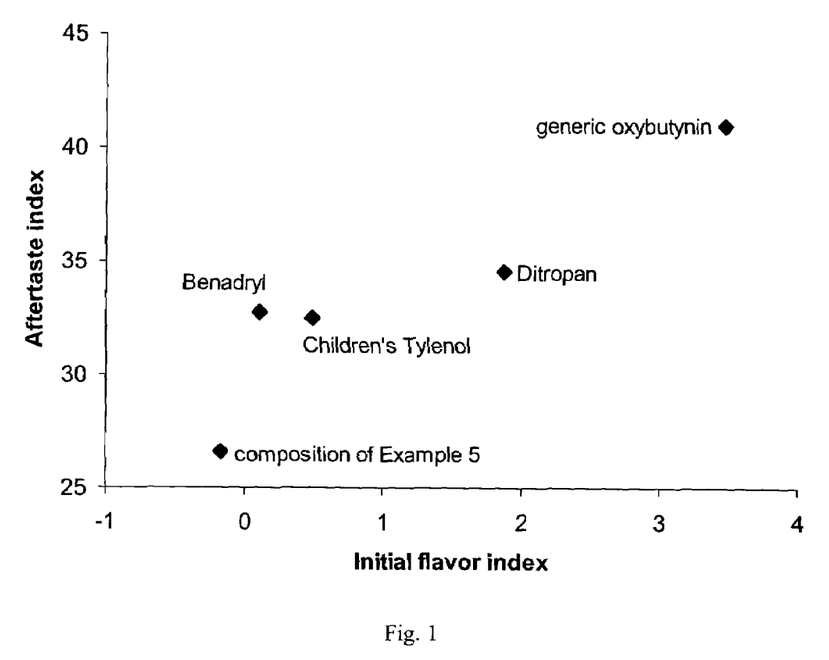
FIG. 1 is a graphical representation of data comparing palatability of the composition of Example 5 with comparator compositions, as described in Example 15.

Results of the study are summarized in FIG. 1, which visualizes differences between the composition of the invention (Example 5) and the comparators on a two-dimensional continuum wherein one dimension (represented on the horizontal axis of FIG. 1) represents an initial flavor index and the other dimension (represented on the vertical axis of FIG. 1) represents an aftertaste index. These indices were derived from the individual attribute scores such that the lower the index the better the flavor quality.

As shown in FIG. 1, the composition of the invention exhibited superior flavor quality by comparison with Ditropan® and generic oxybutynin chloride syrups, both in initial flavor index and in aftertaste index. The superior initial flavor arose from the composition of the invention having lower scores than these comparators on the "bitter", "mouth irritation" and "others" attributes, and higher scores on the "balance" and "aromatics" attributes. The superior aftertaste arose from the composition of the invention having lower scores than these comparators on the "bitter", "mouth irritation" and "others" attributes.

The composition of the invention was also at least comparable to the Tylenol® and Benadryl® comparators in initial flavor quality and superior in aftertaste.

These results represent a surprisingly favorable palatability profile for a composition of the invention, indicating a significant advance in the art, especially in providing an effective treatment for overactive bladder with potential for a high degree of patient compliance.

Tolterodine L-tartrate solutions more concentrated than those tested in Example 15, in addition to bitter taste have an astringent effect on the oral mucosa. Astringency is more difficult to mask than bitterness by addition of sweeteners. It has been discovered that astringency of an aqueous solution of tolterodine L-tartrate is marginally acceptable at a concentration of 1.0 mg/ml, therefore it is contemplated that the concentration should not exceed about 1 mg/ml, preferably about 0.8 mg/ml, most preferably about 0.4 mg/ml, in a composition of the invention. However, as tolterodine is a very potent drug, such low concentrations permit administration of a therapeutically effective amount of tolterodine in a relatively small volume of a liquid composition.

Example 16

Tolterodine has been found to be unstable in aqueous solutions of tolterodine salts at alkaline pH and has optimum stability at a pH of about 4. Because most pharmaceutically acceptable antimicrobials are not fully effective in acid conditions, tests were conducted on compositions similar to those of Examples 4, 5 and 6 but with varying amounts of sodium benzoate, to determine the level of antimicrobial needed to show acceptable antimicrobial effect.

Antimicrobial Effectiveness Testing (AET) results are presented in Tables 15–26. Tests were conducted according to *United States Pharmacopeia* (2000), 24th edition (USP 24), test 51, Antimicrobial testing; and EP 5.1.3, Efficacy of antimicrobial preservation. By varying the amount of antimicrobial, the minimum concentration of the antimicrobial, in this case sodium benzoate, was determined below which antimicrobial properties of the composition become compromised. Tables 15–17 show AET (pass or fail) results for the modified compositions of Examples 4, 5 and 6, and Tables 18–26 give reductions in microbial counts (expressed as logarithm) for each composition.

TABLE 15

AET results for the composition of Example 4 with varying sodium benzoate concentration

| sodium benzoate (mg/ml) | AET result |
| --- | --- |
| 0 | Fail |
| 0.5 | Fail |
| 1 | Pass |

TABLE 16

AET results for the composition of Example 5 with varying sodium benzoate concentration

| sodium benzoate (mg/ml) | AET result |
| --- | --- |
| 0.6 | Pass |
| 0.75 | Pass |
| 1 | Pass |

TABLE 17

AET results for the composition of Example 6 with varying sodium benzoate concentration

| sodium benzoate (mg/ml) | AET result |
| --- | --- |
| 0.6 | Pass |
| 0.75 | Pass |
| 1 | Pass |

TABLE 18

Logarithmic counts in composition of Example 4, modified to contain no sodium benzoate

| Isolate | Initial count | Day 0 | Day 14 | Day 28 |
| --- | --- | --- | --- | --- |
| S. aureus | 6.8 | 0.2 | >5.8 | >5.8 |
| P. aeruginosa | 6.9 | 0.1 | >5.9 | >5.9 |
| E. coli | 6.8 | 0.2 | 5.8 | >5.8 |
| C. albicans | 5.6 | 0.3 | −0.2 | 0.2 |
| A. niger | 5.9 | 0.2 | 0.9 | 0.2 |
| Pseudomonas sp. | 7.4 | 0 | >6.4 | >6.4 |
| P. cepacia | 6.7 | 0 | >5.7 | >5.7 |
| Corynebacterium sp. | 7.1 | 0.3 | 1.4 | >6.1 |
| Penicillium sp. | 5.1 | 0.2 | 0.2 | −0.5 |
| Z. rouxii | 5.6 | 0.2 | 0.2 | −0.1 |

TABLE 19

Logarithmic counts in composition of Example 4, modified to contain 0.5 mg/ml sodium benzoate

| Isolate | Initial count | Day 0 | Day 14 | Day 28 |
| --- | --- | --- | --- | --- |
| S. aureus | 6.8 | 0.2 | >5.8 | >5.8 |
| P. aeruginosa | 6.9 | 0.1 | >5.9 | >5.9 |
| E. coli | 6.8 | 0.2 | >5.8 | >5.8 |
| C. albicans | 5.6 | 0.2 | >4.6 | >4.6 |
| A. niger | 5.9 | 0.2 | 3.6 | 3.6 |
| Pseudomonas sp. | 7.4 | 0 | >6.4 | >6.4 |
| P. cepacia | 6.7 | 0.3 | >5.7 | >5.7 |
| Corynebacterium sp. | 6.7 | 0.5 | >5.7 | >5.7 |
| Penicillium sp. | 5.1 | 0.1 | 1.4 | 1.2 |
| Z. rouxii | 5.6 | 0.1 | >4.6 | 1.5 |

TABLE 20

Logarithmic counts in composition of Example 4, containing 1 mg/ml sodium benzoate

| Isolate | Initial count | Day 0 | Day 14 | Day 28 |
|---|---|---|---|---|
| S. aureus | 6.8 | 0 | >5.8 | >5.8 |
| P. aeruginosa | 6.9 | 0.1 | >5.9 | >5.9 |
| E. coli | 6.8 | 0.2 | >5.8 | >5.8 |
| C. albicans | 5.6 | 0.3 | >4.6 | >4.6 |
| A. niger | 5.9 | 0.2 | >4.9 | >4.9 |
| Pseudomonas sp. | 7.4 | 0 | >6.4 | >6.4 |
| P. cepacia | 6.7 | 0.3 | >5.7 | >5.7 |
| Corynebacterium sp. | 7.1 | 0.2 | >6.1 | >6.1 |
| Penicillium sp. | 5.1 | 0.1 | >4.1 | >4.1 |
| Z. rouxii | 5.6 | 0 | >4.6 | >4.6 |

TABLE 21

Logarithmic counts in composition of Example 5, modified to contain 0.6 mg/ml sodium benzoate

| Isolate | Initial count | Day 0 | Day 14 | Day 28 |
|---|---|---|---|---|
| S. aureus | 6.7 | 0.1 | >5.7 | >5.7 |
| P. aeruginosa | 6.7 | 0.2 | >5.7 | >5.7 |
| E. coli | 6.5 | −0.1 | >5.5 | >5.5 |
| C. albicans | 5.9 | 0.2 | >4.9 | >4.9 |
| A. niger | 5.9 | 0.1 | 2.4 | 3.4 |
| Pseudomonas sp. | 6.9 | 0.1 | >5.9 | >5.9 |
| P. cepacia | 6.4 | 0.6 | 4.0 | >5.4 |
| Corynebacterium sp. | 6.9 | 1.1 | >5.9 | >5.9 |
| Penicillium sp. | 5.6 | 0.4 | >4.6 | >4.6 |
| Z. rouxii | 5.7 | 0 | >4.7 | >4.7 |

TABLE 22

Logarithmic counts in composition of Example 5, modified to contain 0.75 mg/ml sodium benzoate

| Isolate | Initial count | Day 0 | Day 14 | Day 28 |
|---|---|---|---|---|
| S. aureus | 6.7 | 0.1 | >5.7 | >5.7 |
| P. aeruginosa | 6.7 | 0.2 | >5.7 | >5.7 |
| E. coli | 6.5 | −0.1 | >5.5 | >5.5 |
| C. albicans | 5.9 | 0.2 | >4.9 | >4.9 |
| A. niger | 5.9 | 0.1 | 2.4 | 3.4 |
| Pseudomonas sp. | 6.9 | 0.1 | >5.9 | >5.9 |
| P. cepacia | 6.4 | 0.6 | 4.0 | >5.4 |
| Corynebacterium sp. | 6.9 | 1.1 | >5.9 | >5.9 |
| Penicillium sp. | 5.6 | 0.4 | >4.6 | >4.6 |
| Z. rouxii | 5.7 | 0 | >4.7 | >4.7 |

TABLE 23

Logarithmic counts in composition of Example 5, containing 1 mg/ml sodium benzoate

| Isolate | Initial count | Day 0 | Day 14 | Day 28 |
|---|---|---|---|---|
| S. aureus | 6.7 | −0.2 | >5.7 | >5.7 |
| P. aeruginosa | 6.7 | 0.1 | >5.7 | >5.7 |
| E. coli | 6.5 | −0.1 | >5.5 | >5.5 |
| C. albicans | 5.9 | 0.2 | >4.9 | >4.9 |
| A. niger | 5.9 | 0.1 | >4.9 | >4.9 |
| Pseudomonas sp. | 6.9 | 0.2 | >5.9 | >5.9 |
| P. cepacia | 6.4 | 0.8 | >5.4 | >5.4 |
| Corynebacterium sp. | 6.9 | 0.2 | >5.9 | >5.9 |
| Penicillium sp. | 5.6 | 0.2 | >4.6 | >4.6 |
| Z. rouxii | 5.8 | 0.1 | >4.8 | >4.8 |

TABLE 24

Logarithmic counts in composition of Example 6, modified to contain 0.6 mg/ml sodium benzoate

| Isolate | Initial count | Day 0 | Day 14 | Day 28 |
|---|---|---|---|---|
| S. aureus | 6.8 | 0.3 | >5.8 | >5.8 |
| P. aeruginosa | 6.7 | 0.2 | >5.7 | >5.7 |
| E. coli | 6.6 | −0.2 | >5.6 | >5.6 |
| C. albicans | 5.7 | 0 | 3.2 | >4.7 |
| A. niger | 5.9 | 0.1 | 3.4 | >4.9 |
| Pseudomonas sp. | 6.6 | 0.1 | >5.6 | >5.6 |
| P. cepacia | 6.0 | 0.3 | >5.0 | >5.0 |
| Corynebacterium sp. | 6.7 | 0.1 | >5.7 | >5.7 |
| Penicillium sp. | 5.4 | 0 | >4.4 | >4.4 |
| Z. rouxii | 5.8 | 0.1 | 3.2 | 4.2 |

TABLE 25

Logarithmic counts in composition of Example 6, modified to contain 0.75 mg/ml sodium benzoate

| Isolate | Initial count | Day 0 | Day 14 | Day 28 |
|---|---|---|---|---|
| S. aureus | 6.8 | 0.2 | 5.5 | >5.8 |
| P. aeruginosa | 6.7 | 0.1 | >5.7 | >5.7 |
| E. coli | 6.6 | −0.3 | >5.6 | >5.6 |
| C. albicans | 5.7 | −0.1 | 3.6 | >4.7 |
| A. niger | 5.9 | 0 | 4.9 | >4.9 |
| Pseudomonas sp. | 6.6 | 0.2 | >5.6 | >5.6 |
| P. cepacia | 6.0 | 0.4 | >5.0 | >5.0 |
| Corynebacterium sp. | 6.7 | 0.2 | >5.7 | >5.7 |
| Penicillium sp. | 5.4 | 0.2 | 4.4 | >4.4 |
| Z. rouxii | 5.8 | 0 | >4.8 | >4.8 |

TABLE 26

Logarithmic counts in composition of Example 6, containing 1 mg/ml sodium benzoate

| Isolate | Initial count | Day 0 | Day 14 | Day 28 |
|---|---|---|---|---|
| S. aureus | 6.8 | 0.1 | >5.8 | >5.8 |
| P. aeruginosa | 6.7 | 0 | >5.7 | >5.7 |
| E. coli | 6.6 | −0.2 | >5.6 | >5.6 |
| C. albicans | 5.7 | −0.1 | 4.4 | >4.7 |
| A. niger | 5.9 | 0.1 | >4.9 | >4.9 |
| Pseudomonas sp. | 6.6 | 0.1 | >5.6 | >5.6 |
| P. cepacia | 6.0 | 0.4 | >5.0 | >5.0 |
| Corynebacterium sp. | 6.7 | 0 | >5.7 | >5.7 |
| Penicillium sp. | 5.4 | 0.4 | >4.4 | >4.4 |
| Z. rouxii | 5.8 | 0 | >4.8 | >4.8 |

The invention claimed is:

1. A pharmaceutical composition in a form of an orally deliverable liquid, the composition comprising water having in solution therein a pharmaceutically acceptable water-soluble salt of a tolterodine related compound" herein is tolterodine, (R)-N,N-diisopropyl-3-(2-hydroxy-5-methylphenyl)-3-phenylpropanamine, its (S)-enantiomer or a racemic mixture thereof; a metabolite thereof that exhibits antimuscarinic activity, including (R)-N,N-diisopropyl-3-(2-hydroxy-s-hydroxmethylphenyl)-3-phenylpropanamle (herein "hydroxytolterodine"), its (S)-enantiomer or a racemic mixture thereof; or a prodrug of tolterodine, hydroxytolterodine, the (S) enantiomers or racemic mixtures. A preferred such compound is tolterodine at a therapeutically effective concentration in the composition; wherein the composition has a pH of about 2 to about 6 and further comprises a sweetening agent and an antimicrobial agent at a concentration that is antimicrobially effective at the pH of the composition.

2. The composition of claim 1 that comprises means for adjusting pH to about 2 to about 5.

3. The composition of claim 2 wherein the pH adjusting means comprises an acidic buffer system.

4. The composition of claim 1 wherein the salt has a solubility in water of at least 10 mg/ml.

5. The composition of claim 1 wherein the salt has a solubility in water of at least 10 mg/ml.

6. The composition of claim 1 wherein the tolterodine related compound is hydroxytolterodine.

7. The composition of claim 1 wherein the tolterodine related compound is tolterodine.

8. The composition of claim 7 wherein the salt of tolterodine is selected from the heptanoate, caprate, laurate, edisylate, pamoate, xinafoate, 2-hydroxy-1-naphthoate, maleate, fumarate, benzoate, tartrate, hydrochloride, hydrobromide, hydroiodide, sulfate, phosphate, nitrate, citrate and mesylate salts.

9. The composition of claim 7 wherein the salt of tolterodine is tolterodine tartrate.

10. The composition of claim 9 wherein the concentration of tolterodine tartrate is about 0.01 to about 1 mg/ml.

11. The composition of claim 9 wherein the concentration of tolterodine tartrate is about 0.05 to about 0.8 mg/ml.

12. The composition of claim 9 wherein the concentration of tolterodine tartrate is about 0.1 to about 0.4 mg/ml.

13. The composition of claim 7 wherein the pH is about 3 to about 5.

14. The composition of claim 7 wherein the pH is about 3.5 to about 4.5.

15. The composition of claim 7 that comprises an acidic buffer system effective to achieve a pH of about 3 to about 5.

16. The composition of claim 7 that comprises an acidic buffer system effective to achieve a pH of about 3.5 to about 4.5.

17. The composition of claim 15 wherein the acidic buffer system comprises an acidulant acid and an alkali metal salt of said acid.

18. The composition of claim 15 wherein the acidic buffer system comprises an citric acid and sodium citrate.

19. The composition of claim 7 wherein the antimicrobial agent is selected from the group consisting of sorbic and benzoic acids and salts thereof.

20. The composition of claim 7 wherein the antimicrobial agent is sodium benzoate.

21. The composition of claim 20 wherein the sodium benzoate is present in a concentration in the composition of about 0.6 to about 2 mg/ml.

22. The composition of claim 20 wherein the sodium benzoate is present in a concentration in the composition of about 0.7 to about 1.5 mg/ml.

23. The composition of claim 7 wherein the sweetening agent is selected from the group consisting of glucose, fructose, sucrose, xylitol, tagarose, sucralose, maltitol, isomaltulose, hydrogenated isomaltulose, lactitol, sorbitol, mannitol, trehalose, polydextrose, glycerin, erythritol, acesulfame and salts thereof, alitame, aspartame, neotame, cyclamate, saccharin and salts thereof, neohesperidin dihydrochalcone, stevioside, thaumatin, hydrogenated starch hydrolysates, high fructose corn syrup and combinations thereof.

24. The composition of claim 7, further comprising a flavoring agent.

25. A method of treating a muscarinic receptor mediated disorder in a subject, the method comprising orally administering to the subject a therapeutically effective dosage amount of the composition of claim 1.

26. The method of claim 25 wherein the disorder is overactive bladder.

27. The method of claim 25 wherein the dosage amount is not greater than about 20 ml.

28. The method of claim 25 wherein the composition comprises tolterodine tartrate and the dosage amount delivers about 0.2 to about 5 mg of the tolterodine tartrate.

29. The method of claim 28 wherein the dosage amount delivers about 1 to about 2 mg of the tolterodine tartrate.

30. The method of claim 25 wherein the composition is administered 1 to 2 times daily.

* * * * *